United States Patent [19]

Kereluk

[11] 4,087,326
[45] May 2, 1978

[54] MICROBIOLOGICAL SCALED STERILITY TEST STRIPS AND METHOD

[75] Inventor: Karl Kereluk, Basking Ridge, N.J.

[73] Assignee: Ethicon, Inc., Somerville, N.J.

[21] Appl. No.: 682,009

[22] Filed: May 3, 1976

[51] Int. Cl.² .............................................. C12K 1/00
[52] U.S. Cl. .............................. 195/103.5 R; 195/127
[58] Field of Search ......... 195/103.5 R, 127, 103.5 M

[56] References Cited

U.S. PATENT DOCUMENTS

| | | | |
|---|---|---|---|
| 3,107,204 | 10/1963 | Brown et al. | 195/103.5 R |
| 3,341,427 | 9/1967 | Evans et al. | 195/103.5 R |
| 3,346,464 | 10/1967 | Ernst | 195/103.5 R |
| 3,711,378 | 1/1973 | Kereluk | 195/103.5 R |
| 3,819,490 | 6/1974 | Klingstrom et al. | 195/103.5 R |

*Primary Examiner*—Raymond N. Jones
*Assistant Examiner*—Robert J. Warden

*Attorney, Agent, or Firm*—Wayne R. Eberhardt

[57] ABSTRACT

A method and apparatus for obtaining a permanent visual record of the microbiological effectiveness of a sterilizing cycle is provided by a spore carrier strip having a plurality of individual spore colony sites defined on the surface thereof, each of said sites containing a different population of spores, as for example, $10^2$, $10^3$, $10^4$, $10^5$, and $10^6$. The spore carrier is exposed to the sterilizing cycle, then incubated in a sterile nutrient culture medium containing a color indicator for viable microorganisms such as 2,3,5-triphenyl tetrazolium chloride. The development or lack of development of color on each spore colony site of successively increasing spore populations indicates the degree of effectiveness of the sterilizing cycle. The developed color is permanent and the carrier strip may be retained to provide a permanent visual record of the effectiveness of the sterilizing cycle.

10 Claims, 7 Drawing Figures

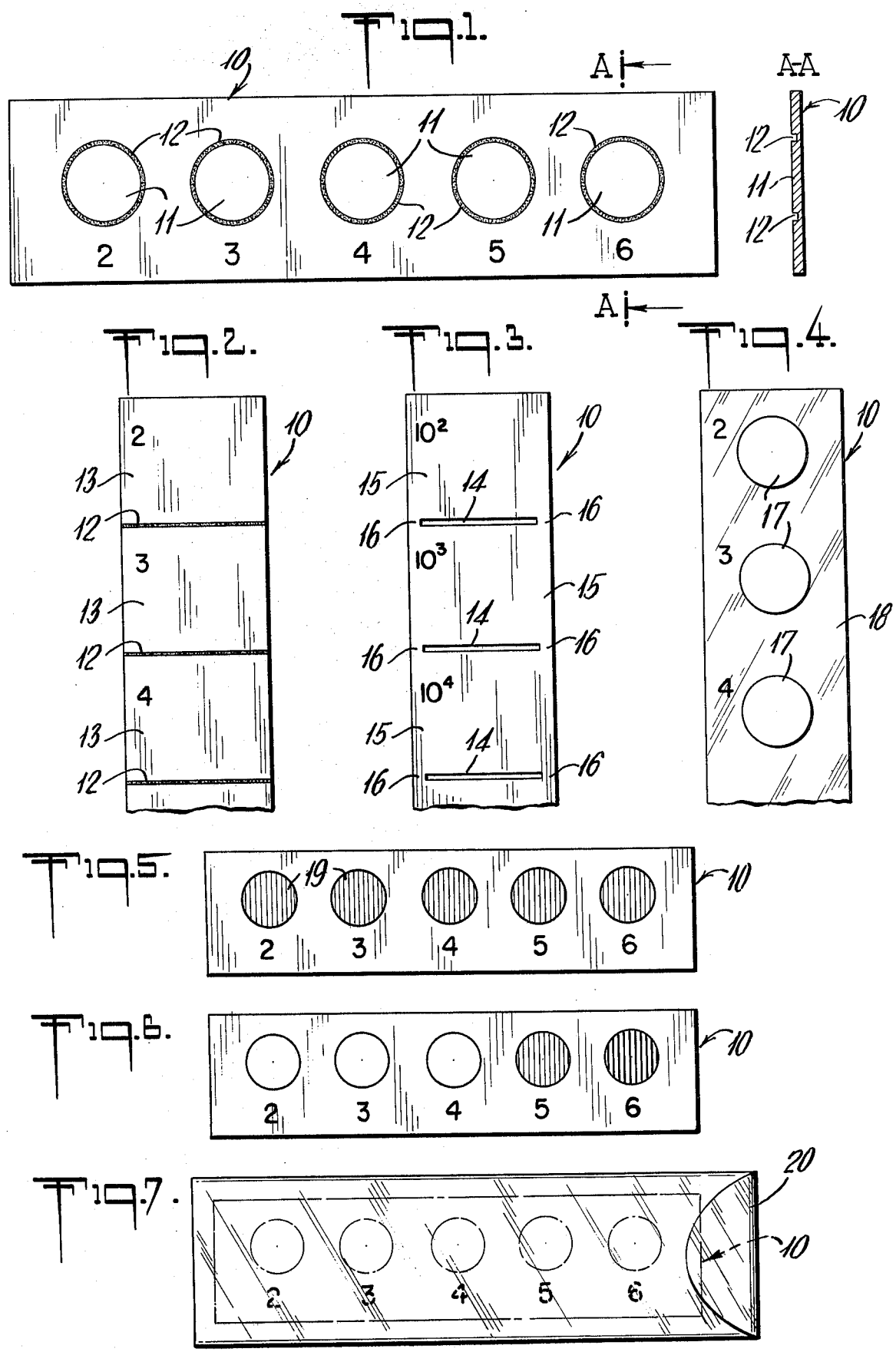

MICROBIOLOGICAL SCALED STERILITY TEST STRIPS AND METHOD

BACKGROUND OF THE INVENTION

1. Field of the Invention

This invention relates to a method and apparatus for determining the effectiveness of a sterilization procedure, and more particularly to a biological sterility indicator providing a permanent visual record of the degree of effectiveness of the sterilization procedure.

2. Description of Prior Art

Surgical devices such as sutures, catheters, gloves, bandages, and the like are generally sterilized by the manufacturer so they are ready for use when delivered to the hospital. Sterilizing media such as steam, dry heat, sterilizing gases and radiation have been successfully employed. Problems have arisen, however, in determining the completeness or efficacy of sterilization procedures. It is highly desirable that means be provided whereby the efficacy of a sterilization cycle may be determined quickly and reliably, and without undue laboratory manipulations.

Heretofore, in one known method of sterilization testing, a source of live microbial spores contained on a piece of absorbent paper was placed in a sterilization chamber along with the objects to be sterilized. Upon completion of sterilization, the absorbent paper was removed and placed in a culture medium and the latter transferred to an incubator to develop the microorganisms in the culture. After several days, the culture medium was examined and tested to determine if any of the organisms survived the sterilization. This method not only required a high degree of skill and care in aseptic handling and evaluation of the culture medium, but also several days were required to develop the culture to the extent that a determination of spore survival could be made. Moreover, once the test was completed, the cultures were discarded and no record other than the observations of the analyst remained for future reference.

In most instances, the sterility test utilized a particular microorganism and concentration which was required to be completely killed in order for the sterilization cycle to be acceptable. More recently, Kereluk U.S. Pat. No. 3,711,378 proposed a system wherein a plurality of test strips, each containing different spore populations, were subjected to the sterilization cycle. After sterilization, the strips were removed and incubated in a culture medium to promote the growth of any surviving spores. The effectiveness of the sterilization cycle was determined according to the spore strip containing the highest population which was determined to be completely sterile after the sterilization cycle. Although this represented an improvement over the single test systems of the prior art, it nevertheless required multiple culture media and vessels and extended time to develop the culture medium after the sterilization cycle, and further required subjective evaluation by the analyst with no independent permanent record of the effectiveness of the sterilization being provided for future reference.

It is accordingly an object of the present invention to avoid and overcome the foregoing and other difficulties of the prior art practices.

It is a further object of this invention to provide a single sterility test strip which will indicate the degree of effectiveness of a sterilization cycle in terms of maximum microorganism concentrations killed by the cycle.

It is another object of this invention to provide a method and apparatus for providing a permanent visible record of the effectiveness of a sterilization cycle.

These and other objects of the present invention will be apparent from the ensuing description and claims.

SUMMARY

A spore carrier strip is provided with a plurality of individual, isolated spore colony sites. Each site is inoculated with a predetermined population of spores, preferably in a sequential log scale. The inoculated spore strip is exposed to a sterilization cycle, and thereafter incubated in a sterile nutrient culture medium containing an indicator which will undergo a color change in response to the growth of the microorganisms. The site of greatest spore population showing no color development indicates the degree of effectiveness of the sterilizing cycle. After culturing, the test strip may be removed from the culture medium, washed, dried, and retained as a permanent visual record of the effectiveness of the sterilizing cycle.

DESCRIPTION OF DRAWINGS

FIG. 1 is a spore strip having five (5) individual circular spore colony sites on the surface thereof.

FIG. 2 is a spore strip wherein adjacent spore colony sites are separated by slits cut in the spore strip.

FIG. 3 is a spore strip wherein adjacent spore colony sites are separated by channels printed across the width of the strip.

FIG. 4 is a spore strip wherein individual porous spore colony sites are mounted on a nonporous plastic backing strip.

FIG. 5 is a spore strip of FIG. 1 illustrating color development before sterilization.

FIG. 6 is a spore strip of FIG. 1 illustrating typical color development after sterilization.

FIG. 7 illustrates a spore strip in a glassine envelope.

DESCRIPTION OF THE PREFERRED EMBODIMENTS

The sterility test strips of the present invention are hereinafter sometimes referred to as "spore strips" or as containing "spore colony sites." While reference is thereby made to spores as the test microorganisms, it is understood that microorganisms other than spore formers may be used in conjunction with the sterility test strips.

By "microorganisms," reference is made to bacteria, fungi, yeasts, protozoa, viruses and the like, e.g., microorganisms which may be killed by sterilization. Bacteria and fungi which exist in both "spore" and "vegetative" states are commonly most resistant to sterilization in the spore state. Hence, to provide a margin of safety, bacteria and fungi in the spore state are preferably used in the present invention. Spore preparations of the following bacterial spore forming species useful in the present invention include *Bacillus subtilis, Bacillus stearothermophilus, Bacillus pumilus, Clostridium sporogenes*, etc. Fungal spores which may be employed in the present invention include Neurospora, Pithomyces, and Daldinia, etc.

The spore strips of the present invention are preferably constructed of an absorbent material which is inert to microorganisms, and most conveniently of an absorbent filter paper such as Whatman No. 47. Other absorbent materials such as cloth, threads and sutures, and nonabsorbent materials such as metal foil (e.g., aluminum or stainless steel), glass, porcelain, ceramic, and the like may be also used. Spore strips can also be constructed of a combination of materials such as paper spore colony sites secured to a plastic or glass backing strip. The spore strips may be of any convenient size, but strips 90 mm. long by about 20 mm. wide are particularly preferred for convenience in physically fitting into a standard test tube for later culturing.

The spore colony sites on the spore strip must be isolated from each other to prevent spores from migrating between adjacent sites and interfering with the determination of sterilization efficiency. Isolation of spore sites may be effectively accomplished by any number of methods. For example, barrier lines may be printed on the spore strip under pressure and with a nontoxic ink. Alternatively, the barriers may consist of open slots cut into the spore strip between colony sites, or porous spore colony sites may be adhesively attached to a nonporous backing strip which inhibits spore migration.

Referring now to the drawings, FIG. 1 shows a preferred embodiment wherein circular spore colony sites 11 are defined by rings 12 printed onto the surface of a paper spore strip 10 with a nontoxic ink and under sufficient pressure to permanently compress the paper of the spore strips in the area of the printed line, as illustrated in cross-section A—A.

FIG. 2 shows an alternative embodiment wherein lines 12 are printed across the width of the spore strip 10 to define individual rectangular spore sites 13.

FIG. 3 illustrates a further variation wherein slots 14 are cut into the spore strip 10 between adjacent rectangular spore sites 15 to effectively isolate adjacent sites except for end margins 16 of the strips.

FIG. 4 illustrates another variation wherein spore strip 10 consists of spore colony sites 17 comprised of paper disks individually mounted on a plastic backing strip 18. The physical separation of the spore sites assures that no migration between adjacent sites can occur.

Where printed barriers are used, the printing may be with any nontoxic ink, resin, wax, polymer such as silicone or Teflon, or other material which is effective to close the pores of the spore carrier material and prevent migration of spores across or through the carrier from one spore colony site to another.

As a matter of convenience for ready identification of the population of the individual spore colony sites, an identifying number is preferably printed on the spore strip adjacent each spore colony site. Where the spore colony populations are in a log sequence, e.g., $10^2$, $10^3$, $10^4$, etc., the exponential number only may be printed adjacent to the site as illustrated for example in FIG. 1. Alternatively, the entire value of $10^e$ may be printed on the site as illustrated in FIG. 2. Other identifying information or codes as, for example, identification of the spore or the conditions of sterilization may also be printed directly onto the spore strip.

Once the spore strip has been prepared, it is sterilized by heat or other convenient means effective to destroy any vagrant microorganisms. Individual colony sites on the sterile strips are then inoculated with the desired predetermined populations of spores in accordance with conventional procedures. The spore impregnated strips employed in the method of the present invention are prepared in a manner similar to that currently used for conventional spore strips and described in U.S. Pat. No. 3,711,378, incorporated herein by reference, with the exception that instead of impregnating each strip with only one spore population, several individually defined spore colony sites on a single strip are inoculated with different spore populations.

In practice, the inoculated spore carrier strips are sealed in a glassine envelope as shown in FIG. 7 and exposed either directly to the sterilization process or placed in among the materials or items to be sterilized. The sterilization process is conducted in the usual manner following which the strips are removed from the glassine envelope and cultured in tubes of a bacteriological culturing medium containing a color indicator for viable microorganisms.

The bacteriological culture medium is preferably a solution of Trypticase Soy Broth (TSB) (a product of Bioquest) or Tryptic Soy Broth (a product of Difco Laboratories, Inc.). The tubes are incubated for a time sufficient for the viable spore color indicator to detect the presence of spores which survived the sterilization cycle and respond by visible color development on the spore colony site. In general, incubation at 37° C for a period of about 24 hours is sufficient for visual identification of the presence of surviving spores.

The "viable spore color indicator" may be any indicator such as a pH indicator, an oxidation-reduction indicator, or an enzymatic indicator which will undergo a color change in response to the growth of microorganisms or the presence of their enzymes, by-products, and/or metabolites. Suitable color indicators are known in the art as described for example in U.S. Pat. No. 3,661,717. An indicator which is particularly preferred because of the permanent, vivid red color formed in the presence of viable microorganisms is 2,3,5 - triphenyl tetrazonium chloride (TTC). The incorporation of TTC in the culture medium for obtaining pigmented colonies of microbial organisms has been reported in Jour. Bact. 66 (2), 240–242 (1953). This article also reports TTC exhibits toxicity toward some bacteria and that concentrations must be controlled at levels which are sufficient to produce coloration without inhibiting spore outgrowth.

Maximum acceptable concentrations of TTC in the culture medium will depend to a great extent on the identification of the microorganisms and their resistance to TTC. Optimum concentrations are readily determined by simple experimental tests wherein the microorganisms are exposed to increasing concentrations of TTC and the effect on the growth of the organisms noted. In the Jour. Bact. article supra, growth and maximum pigmentation of colonies of Gram positive and acid-fast bacteria and actinomycetes were obtained at concentrations of TTC up to 0.001%. Concentrations of 0.05% were reported as effectively inhibiting the growth of the acetinomycetes, while the Gram negative bacteria were not inhibited until concentrations of 0.1 to 1.0% were reached.

When using spores of *Bacillus subtilis* var. *niger* as the test microorganism, TTC concentrations in TSB culture medium of from about 0.0005 to 0.05% were found to give good color development with minimal growth inhibition. Concentrations of 0.1% TTC demonstrated complete inhibitory action against growth of spore populations up to $10^6$, while 0.01% retarded growth of $10^6$ populations and completely inhibited growth of $10^2$ populations. Concentrations of 0.005% produced intense coloration at $10^2$ and higher population levels after 24 hours of incubation. Concentrations as low as 0.0005% produced microscopically visible color development with no apparent growth inhibition in a 24-hour culture test. A concentration of 0.0025% was particularly preferred for optimum color development with minimal growth inhibition in the TTC-TSB system using spores of *B. subtilis* var. *niger* microorganisms.

The TTC-TSB culture medium is preferably prepared by aseptically adding TTC, sterilized by filtration through a 0.22u membrane filter, to TSB which has been sterilized by autoclaving. Sterilization of TTC or TTC-TSB mixtures by autoclaving is not recommended since such a procedure has been found to adversely affect subsequent TTC color development.

When the inoculated spore strip is subjected to sterilization conditions, the lower spore populations are more easily destroyed, and the highest spore population which is completely destroyed indicates the degree of effectiveness of the sterilization cycle. FIGS. 5 and 6 illustrate a typical response of the test strips of the present invention to a sterilization cycle. In FIG. 5 an inoculated test strip was cultured without sterilization. The uniform color development on spore colony sites 19 shows all sites contain significant populations of viable microorganisms. In FIG. 6, color development after sterilization is limited to the $10^5$ and $10^6$ spore colonies indicating effective sterilization of moderately high $10^4$ spore populations had been achieved. Articles treated or exposed to the sterilization cycle with the test strip could be accepted or rejected on the basis of the adequacy of a $10^4$ effective sterilization.

The following specific example is provided for the purpose of illustrating the preparation and use of the scaled sterility test strips in accordance with the present invention. It is understood that this example serves by way of illustration only and is not intended to limit the invention to the precise materials shown nor the application and use thereof.

EXAMPLE

A number of sterility test strips were prepared by cutting strips of Whatman No. 47 filter paper 90 mm. by 19 mm. and having five rings printed thereon as illustrated in FIG. 1. Each ring formed a spore colony site having a border approximately 1 mm. wide encircling a central area having a diameter of approximately 7 mm. The test strips were heat sterilized and the central area of each spore colony site inoculated with 10 ul of an aqueous suspension of *B. subtilis* var. *niger* in a concentration to provide a log series of spore populations from $10^4$ and $10^8$ on the spore colony sites.

The inoculated sterility test strips were placed in a sterile glassine envelope and sterilized under dry heat at 150° C for 5, 10, 15, 30 and 60 minutes. The sterilized strips were removed from the glassine envelopes and cultured in an incubator for 24 hours at 37° C in a sterile solution of TSB containing 0.0025% TTC. An unsterilized control strip demonstrated vivid red color development in sites $10^6$ through $10^8$, with light color in $10^4$ and $10^5$. In strips exposed for 5 minutes, color remained dark in sites $10^7$ and $10^8$, light in $10^5$ and $10^6$, while $10^4$ appeared clear. In strips exposed for 10 minutes, light color was evident in $10^7$ and $10^8$, while $10^4$ through $10^6$ appeared clear. In strips exposed for 15 minutes, a trace of color was still evident in $10^8$, but $10^4$ through $10^7$ appeared clear. In strips exposed for 30 and 60 minutes, no color development was observed in any spore colony site. After culturing, the spore strips were washed and dried to form a permanent record of the effectiveness of each sterilization exposure.

Interpretation of the above results indicates that 15 minutes of dry heat at 150° C is capable of destroying high concentrations of spore populations up to the $10^7$ level. A single sterility test strip included with each batch of articles to be sterilized would provide a permanent visible record of the effectiveness of the sterilization cycle to which the articles were subjected. Where a batch of articles are sterilized in large numbers or stacked pallets or on racks, several sterility test strips distributed throughout the articles provide a measure of the uniformity of sterilization throughout the batch.

The preceding example was repeated using 1200 mg of ethylene oxide per liter of air at 88° F and 40–60% relative humidity as the sterilizing agent and with 0, 10, 20, and 30 minutes exposure times. Test strip color development indicated that 20 minutes exposure was effective to sterilize $10^6$ spore populations. Comparable results are obtained with other methods or agents of sterilization as, for example, steam heat, cobalt 60 ionizing radiation, election beam radiation, microwave radiation and the like.

Although the spore concentrations on the test strips are not limited except by practical considerations, it should be noted with respect to unsterilized viable control systems that high populations of spores of *B. subtilis* var. *niger*, e.g., $10^7$ and $10^8$, appear to have an inhibiting effect on the growth of lower spore populations contained on the same test strip. In the example above, the unsterilized strips containing $10^4$ through $10^8$ spore populations demonstrated only faint color development in the $10^4$ and $10^5$ colonies, and it appears that the spore outgrowth from the higher population centers inhibited the growth of those lower population centers. When the experiment was repeated using a log scale population count from $10^2$ to $10^6$, no inhibition of the lower population colonies was evident. Thus, in a viable control system using *B. subtilis* var. *niger*, a maximum spore population of $10^6$ is preferred. Similar limitations may be required for viable control systems using other species of spore formers.

The present invention, although described herein primarily in terms of a single microbial species (*B. subtilis* var. *niger*) in a number of different concentrations, is also appicable to the use of multiple microorganisms at the same or different concentrations. For example, a single spore strip having 6 spore population sites could be inoculated with two different microorganisms, each at three different concentrations, or inoculated with three different microorganisms, each at two different concentrations.

In addition, scaled sterility test strips may contain a greater or lesser number of spore colony sites in any of a variety of configurations. The basic concept of the present invention resides in providing a number of different spore colonies on a single test strip, and culturing the test strip in a medium containing a viable microorganism or active microbial color indicator, whereby there is obtained a single sterility test strip which provides a visible indication of the degree of effectiveness of the sterilization process. Many variations of this basic concept will be apparent to those skilled in the art and the invention is accordingly not limited to any specific embodiments set forth herein.

What is claimed is:

1. A method for providing a permanent record of the effectiveness of a sterilizing cycle which comprises (a) providing a sterility test strip comprising a single carrier having a plurality of individual microorganism colony sites defined on the surface thereof, each of said sites containing a different population of microorganisms, (b) exposing said sterility test strip to the sterilizing cycle and (c) incubating said colony sites on said exposed test strip in a common culture medium containing a viable microorganism color indicator whereby the effectiveness of the sterilizing cycle is indicated by the degree of color development on the individual microorganism colony sites.

2. A method of claim 1 wherein the concentration of microorganisms in each colony site is equal to a real positive integer greater than zero raised to a real positive exponential integer, each of said exponential integers being different from the others.

3. A method of claim 2 wherein the population of microorganisms on said sites is from $10^2$ to $10^6$.

4. A method of claim 1 wherein the viable microorganism color indicator is a tetrazolium salt.

5. A method of claim 4 wherein the color indicator is 2,3,5-tetrazolium chloride.

6. A method of claim 5 wherein the concentration of 2,3,5-triphenyl tetrazolium chloride in the culture medium is from about 0.0005 to 0.005%.

7. A method of claim 6 wherein the concentration of 2,3,5-triphenyl tetrazolium chloride is about 0.0025%.

8. A method of claim 1 wherein the exposed test strip is incubated in said culture medium for at least about 24 hours at 37° C.

9. A method of claim 1 wherein the culture medium is Trypticase Soy Broth.

10. A method of claim 1 wherein the microorganisms are spores of *Bacillus subtilis.*

* * * * *

UNITED STATES PATENT AND TRADEMARK OFFICE
CERTIFICATE OF CORRECTION

PATENT NO. : 4,087,326
DATED : May 2, 1978
INVENTOR(S) : Karl Kereluk

It is certified that error appears in the above-identified patent and that said Letters Patent are hereby corrected as shown below:

At Column 3, Line 53, "value of $10^e$" should be -- value of $10^3$ --.
At Column 4, Line 33, "tetrazonium" should be -- tetrazolium --.
At Column 4, Line 50, "actinomycetes" should be -- acetinomycetes --.
At Column 4, Line 58, "to 0.05%" should be -- 0.005% --.
At Column 6, Line 8, "numbers or stacked" should be -- numbers on stacked --.
At Column 6, Line 20, "election beam" should be -- electron beam --.
At Claim 5, Line 4, "2,3,5-tetrazolium chloride" should be -- 2,3,5-triphenyl tetrazolium chloride --.

Signed and Sealed this

Twelfth Day of December 1978

[SEAL]

Attest:

RUTH C. MASON
Attesting Officer

DONALD W. BANNER
Commissioner of Patents and Trademarks